United States Patent [19]

Healey

[11] Patent Number: 4,981,685

[45] Date of Patent: Jan. 1, 1991

[54] BACTERIAL EXTRACT VACCINES FOR VETERINARY APPLICATION

[75] Inventor: Mark C. Healey, Logan, Utah

[73] Assignee: Utah State University Foundation, Logan, Utah

[21] Appl. No.: 98,773

[22] Filed: Sep. 17, 1987

Related U.S. Application Data

[63] Continuation of Ser. No. 837,610, Mar. 7, 1986, abandoned.

[51] Int. Cl.$^5$ .................... A61K 37/02; A61K 37/39
[52] U.S. Cl. ......................... 424/92; 405/822; 405/881
[58] Field of Search ............... 424/92; 425/851, 822

[56] References Cited

U.S. PATENT DOCUMENTS

| | | | |
|---|---|---|---|
| 3,149,036 | 9/1964 | Woodhour et al. | 424/92 X |
| 3,172,815 | 3/1965 | Fox et al. | 424/92 |
| 3,395,219 | 7/1968 | Millman | 424/92 |
| 3,594,471 | 7/1971 | Hertzberger et al. | 424/92 X |
| 4,069,314 | 1/1978 | Adlam et al. | 424/92 |
| 4,203,971 | 5/1980 | Buchanan | 424/92 |
| 4,271,147 | 6/1981 | Helting et al. | 424/92 |
| 4,351,761 | 9/1982 | Gaafar | 424/92 X |
| 4,397,838 | 8/1983 | d'Hinterland et al. | 424/92 |
| 4,427,782 | 1/1984 | Caldwell et al. | 530/825 X |
| 4,442,085 | 4/1984 | Colman et al. | 424/92 X |
| 4,443,431 | 4/1984 | Buchanan et al. | 424/92 |
| 4,448,768 | 5/1984 | Colman et al. | 424/92 |
| 4,451,286 | 7/1984 | Hilleman et al. | 424/92 X |
| 4,472,302 | 9/1984 | Karkhanis | 424/92 X |
| 4,474,758 | 10/1984 | Klio et al. | 424/92 |
| 4,493,825 | 1/1985 | Platt et al. | 424/92 X |
| 4,503,036 | 3/1985 | Girardon et al. | 424/92 |
| 4,521,513 | 6/1985 | Russell | 424/92 X |
| 4,578,269 | 3/1986 | Morein | 424/92 X |
| 4,707,543 | 11/1987 | Zollinger et al. | 424/92 X |

OTHER PUBLICATIONS

Chemical & Engineering News, 51-68 (Oct. 5, 1987), Stinson.
Mobay Corporation, Animal Health Division, "New Vaccine for Horses Introduced: Prevents Contagious Respiratory Disease", Haver News Release (Feb. 17, 1986).
Utah State University, "Vaccines, Antibodies Launch New Attack on Bacteria That Cause Sheep Sterility", Outlook, p. 14 (Nov./Dec., 1985).
The Calbiochem Biochemical and Immunochemical Catalog, Calbiochem-Behring, a division of American Hoechst Corporation (1985).
"Detergent Descriptions", Calbiochem-Behring.
Biologics, a Newsletter of Calbiochem-Behring, a division of American Hoechst, vol. 11, No. 5 (Dec., 1985).
Biologics, a Newsletter of Calbiochem-Behring, a division of American Hoechst, vol. 11, No. 4 (Sept., 1985).
Biologics, a Newsletter of Calbiochem-Behring, a division of American Hoechst, vol. 11, No. 2 (Apr., 1985).

"The Vexing Problems of Vaccine Compensation", Science, vol. 227, p. 1012 (Mar., 1985).
P. W. Wells et al., "Development of a Combined Clostridial and *Pastuerella haemolytica* Vaccine for Sheep", The Veterinary Record, vol. 114, pp. 266-269 (Mar., 17, 1984).
Setsuo Saito et al., "Characteristics of n-octyl B-D-thioglucopyranoside, a New Non-Ionic Detergent Useful for Membrane Biochemistry", Biochem. J., vol. 222, pp. 829-832 (1984).
Bacterial Vaccines (Rene' Germanier, ed.), Academic Press, Inc. (1984).
N. J. L. Gilmour et al., "Experimental Immunisation of Lambs Against Penumonic Pasteurellosis", Research in Veterinary Science, vol. 35, pp. 80-86 (1983).
James E. K. Hidreth, "N-D-Gluco-N-Methylalkanamide Compounds, a New Class of Non-Ionic Detergents for Membrane Biochemistry", Biochem. J., vol. 207, pp. 363-366 (1982).
Edith L. Camm et al., "Widespread Distribution of Some Minor Chlorophyll-Protein Complexes in Some Plants and Algae", Plant Physiol., vol. 67, pp. 1061-1063 (1981).
N. J. L. Gilmour et al., "The Development of Vaccines Against Pneumonic Pasteurellosis in Sheep", The Veterinary Record, vol. 111, p. 15 (Jan. 6, 1979).
P. W. Wells et al., "A Serological Comparison of *Pasteurella Haemolytica* Vaccines Containing Different Adjuvants", Research in Veterinary Science, vol. 27, pp. 248-250 (1979).
Carl Baron et al., "Solubilization of Bacterial Membrane Proteins Using Alkyl Glucosides and Dioctanoyl Phosphatidylcholine", Biochemica et Biophysics Acta, vol. 382, pp. 276-285 (1975).
Handbook of Experimental Immunology-Application of Immunological Methods, (D. M. Weir, ed.), Blackwell Scientific Publications, vol. 3, Appendix 3, Third Edition (1978).
"Ribi Biological Response Modifiers".

Primary Examiner—Howard E. Schain
Attorney, Agent, or Firm—Workman, Nydegger & Jensen

[57] ABSTRACT

The present invention relates to novel bacterial extract vaccines for use in veterinary medicine and to novel methods for preparing such vaccines. The bacteria responsible for a particular bacterially induced disease is contacted with a detergent so as to extract from the bacterial cells the antigens responsible for eliciting a protective immune response against the disease. Subsequently, the resultant antigen extract is dialyzed to remove the detergent. The antigen extract is then preferably combined with a vaccine enhancing adjuvant to provide an effective and inexpensive vaccine for veterinary application. The present invention provides for the preparation of a variety of vaccines which can be used to immunize animals against a variety of bacterially induced diseases.

3 Claims, No Drawings

BACTERIAL EXTRACT VACCINES FOR VETERINARY APPLICATION

RELATED APPLICATION

This application is a continuation of U.S. patent application Ser. No. 06/837,610, filed Mar. 7, 1986, for "Bacterial Extract Vaccines For Veterinary Application" by the same inventor, now abandoned.

BACKGROUND

1. The Field of the Invention

The present invention relates to novel bacterial extract vaccines for use in veterinary medicine and to novel methods for preparing such vaccines. The present invention further relates to methods for using the vaccines to immunize animals against a variety of bacterially induced diseases.

2. The Prior Art

Traditionally, bacterial vaccines used in veterinary medicine have been prepared using intact, whole bacterial cells. Necessarily, the bacteria in such bacterial vaccine preparations are severely weakened or killed by such methods as the application of mild heat, cold storage in the presence of thimerosal or formalin, or combinations of these methods. Such alteration of the bacteria is needed in order to reduce, to the greatest extent possible, the risk that the bacteria in the vaccine will produce the corresponding disease once the vaccine has been administered to the animal.

Unfortunately, vaccines prepared from whole bacterial cells are often toxic and produce harmful side effects. This is believed to be due, at least in part, to bacterial endotoxins present in the whole bacterial cells. Thus, although administration of such prior art bacterial vaccines may help to immunize an animal against particular diseases, administration of the prior art vaccines may well result in toxicity and other harmful side effects to the animals vaccinated.

Another disadvantage of many whole bacterial cell vaccines used in the prior art is that such vaccines have frequently been found to produce insufficient immunity in the animals vaccinated. For example, it has been found that whole cell vaccines often do not induce the production of sufficient levels of antibodies to provide adequate long term immunity. This has resulted in less efficient vaccinations and the need to vaccinate the animal populations more frequently.

The development of new animal vaccines against bacterially induced diseases has slowed down significantly in recent years so that the state of the art is only slightly more advanced than it was about 30 years ago. One of the primary reasons for this decline is the ready availability and widespread use of antibiotics in recent years. With the advent of antibiotics, the stimulus for extensive research into antibacterial immunity in veterinary medicine was greatly reduced. However, the situation is now rapidly changing as animals develop resistance to known antibiotics and as the presence of antibiotic residues in food products becomes of increasing concern from the standpoint of public health.

On the other hand, the development of new vaccines in human medicine has moved forward at a much faster pace. Although considerable improvement could still be made with respect to human vaccines, biotechnology and genetic engineering have recently given scientists the capability to refine human vaccines to a very precise level. For example, it is now possible to isolate and purify from a bacterial cell a single desired antigen. Further, once such a specific antigen has been isolated, it is possible to actually map the coding genes and subsequently synthesize that particular antigen in vitro. In this way, essentially unlimited quantities of antigen can be produced for use in human vaccines.

When it comes to vaccines, however, there are important differences between the practice of human medicine and veterinary medicine. For example, human medicine does not envision people's lives in terms of dollars and cents. Thus, the sophisticated antigen synthesis techniques developed for human vaccines are commonly used without regard to cost. With respect to veterinary medicine, however, economic prospects dictate to a large measure the type and extent of vaccination practices which are exercised by animal producers, such as, for example, livestock owners. The result of hard, cold economic reality is that producers cannot afford to use vaccines which are not cost effective. This is particularly true with respect to the production of "minor species" of animals such as sheep and goats.

Therefore, animal vaccine production methods must necessarily be economically realistic if the vaccines are to enjoy widespread usage. Also, the resultant animal vaccines must be effective enough to warrant their use as well as be affordable. Hence, the current sophisticated techniques used for preparing human vaccines are typically cost prohibitive when applied to the preparation of animal vaccines, and other less sophisticated and less expensive methods have been needed in veterinary medicine for preparing economically practical and effective animal vaccines.

In view of the foregoing, it would be a significant advancement in the art of veterinary medicine to provide animal bacterial vaccines which are relatively nontoxic and which substantially avoid the undesirable and harmful side effects of prior art bacterial vaccines. It would be a further significant advancement in the art to provide animal bacterial vaccines which elicit a much stronger immune response in the animals vaccinated than has been characteristic of prior art vaccines. It would be yet another significant advancement in the art to provide relatively simple and inexpensive methods for preparing such bacterial vaccines so as to provide animal vaccines which are both efficacious and affordable. Such bacterial vaccines, such methods for preparing bacterial vaccines, and methods for administering such bacterial vaccines to animals are disclosed and claimed herein.

BRIEF SUMMARY AND OBJECTS OF THE INVENTION

The present invention relates to bacterial vaccines for use in veterinary medicine which are prepared by extracting from the whole bacterial cells antigens responsible for protecting the animal against the bacterially induced disease, and administering only that antigen extract to the animal in the vaccine.

In connection with the present invention, it has been discovered that for most bacterially induced diseases, only a small fraction of the antigens present in the bacterial cell confer immunity to the host, and it is believed that these antigens are primarily present on the bacterial cell surface or outer membrane. Thus, an animal receiving an intact whole bacterial cell suspension vaccine, such as used in the prior art, receives an excess of antigenic and other cellular "garbage" which is immunologically useless to the animal, and which often results in toxicity and harmful side effects. Thus, in the present invention, the antigens responsible for the immune response (which are believed to reside primarily on the surface or outer membrane of the bacterial cells) are extracted from the bacterial cells and concentrated so as to provide animal vaccines which are more efficacious, relatively nontoxic, and which may be isolated by relatively simple and inexpensive extraction procedures.

The presently preferred procedure for preparing bacterial extract vaccines in accordance with the present invention involves primarily two steps: (1) a detergent extraction step and (2) a dialysis step. In the detergent extraction step, the bacteria responsible for the disease to be immunized against are contacted with a detergent which is capable of extracting the antigens responsible for the protective immune response from the bacteria. Subsequently, the resultant antigen extract is dialyzed so as to remove most, and preferably substantially all, of the detergent used in the extraction step. The antigen extract is then preferably combined with a suitable vaccine enhancing adjuvant so as to provide an effective and relatively inexpensive vaccine which can then be administered to the animals to be immunized.

The present invention has wide application in the preparation of a variety of animal vaccines against a variety of bacterially induced diseases.

It is, therefore, an object of the present invention to provide novel bacterial extract vaccines which have particular utility in veterinary medicine.

Another object of the present invention is to provide bacterial extract vaccines which are relatively nontoxic and which may be prepared employing relatively simple and inexpensive procedures.

A further object of the present invention is to provide bacterial extract vaccines which do not include intact, whole bacterial cells, but rather comprise antigens extracted from the bacterial cells, which antigens are responsible for inducing the protective immune response in the vaccinated animal.

Yet another object of the present invention is to provide bacterial extract vaccines for use in veterinary medicine which are both effective and cost justified for the animal producer.

Still another object of the present invention is to provide methods for preparing animal vaccines involving a relatively simple detergent extraction step and a relatively simple dialysis step.

Yet still another object of the present invention is to provide methods which may be used to prepare a wide variety of animal vaccines so as to enable a variety of animals to be vaccinated against a variety of bacterially induced diseases.

A further object of the present invention is to provide bacterial extract vaccines which are more effective in successfully vaccinating animals against bacterially induced diseases than prior art animal vaccines.

These and other objects and features of the present invention will become more fully apparent from the following description and appended claims.

DETAILED DESCRIPTION OF THE PREFERRED EMBODIMENT

In the present invention, it has been discovered that for most bacterially induced diseases, the antigens which are responsible for inducing the protective immune response can be extracted by using a detergent, thereby permitting for selective removal of these important antigens for use in a vaccine. The remaining portions of the bacterial cells from which the antigens are extracted are discarded, thereby providing a vaccine which comprises the required antigens without substantial additional cellular "garbage" which could otherwise prove toxic or harmful to the animal vaccinated.

Moreover, the extracted antigens which are responsible for the protective immune response are concentrated by the extraction process of the present invention, thereby providing a more potent vaccine than afforded by traditional prior art whole cell vaccines. The antigens which are removed by the detergents used in the present invention are believed to reside primarily on the surface or outer membrane of the bacterial cells.

The vaccines of the present invention are intended primarily for use in veterinary medicine. However, it will be understood that the vaccines and methods of the present invention could also be employed in human medicine if desired. Because of the simplicity and relatively inexpensive procedures for preparing the vaccines of the present invention, they are particularly suitable for preparing less sophisticated vaccines which are cost justified to animal producers. However, it will be understood that the present invention is not limited to veterinary application.

With particular regard to veterinary medicine, the present invention may be used to treat most types of animals which may be inflicted by one or more bacterially induced diseases. For example, the following types of animals may be treated using vaccines prepared in accordance with the present invention: cattle, sheep, goats, pigs, and horses. It will be understood that the foregoing list of animals is given by way of example only, and that the foregoing list is therefore not to be considered as comprehensive or exhaustive of the types of animals which may be treated using the present invention.

The present invention may be used to prepare vaccines from virtually any bacteria which contain antigens responsible for eliciting a protective immune response against a corresponding bacterially induced disease once the bacteria find their way into an animal host. Thus, the present invention may be used to prepare a wide variety of vaccines which can be used in the immunization of a wide variety of animals against a wide variety of bacterially induced diseases.

However, it is suspected that the present invention may not be as efficacious in the preparation of bacterial vaccines for the following specific types of diseases: (1) diseases which are mediated by bacterial toxins by actively growing bacterial cells and not by the bacterial cell proper itself, and (2) diseases which require actively growing and dividing bacterial cells in order for the infected host to mount a protective immune response.

Table I below sets forth some of the bacteria from which vaccines may be prepared in accordance with the present invention, along with some of the corresponding diseases induced by those bacteria and against which the vaccines prepared in accordance with the present invention can provide immunization. However, it will be understood that the specific bacteria set forth in Table I below are given by way of example only, and are not to be considered as comprehensive or exhaustive of the types of bacteria which may be employed in the present invention. Thus, it will be appreciated that vaccines which are prepared in accordance with the present invention employing bacteria not set forth in Table I may also be within the scope of the present invention.

TABLE I

| Bacteria | Disease |
|---|---|
| 1. *Neisseria gonorrhoeae* | Gonorrhea |
| 2. *Neisseria menignitidis* | Meningitis |
| 3. *Campylobacter fetus* | Abortion |
| 4. *Klebsiella pneumoniae* | Pneumonia |
| 5. *Escherichia coli* | Diarrhea |
| 6. *Pseudomonas aeruginosa* | Septicemia |
| 7. *Actinobacillus spp* (various strains) | Ram epididymitis |
| 8. *Brucella ovis* | Ram epididymitis |
| 9. *Hemophilus somnus* | Ram epididymitis |
| 10. *Pasteurella spp* (various strains) | Pneumonia, septicemia, and numerous others |
| 11. *Salmonella spp* (various strains) | Gastroenteritis and numerous others |
| 12. *Bacteroides nodosus* | Ovine foot rot |
| 13. *Bordetella bronchiseptica* | Atrophic rhinitis |
| 14. *Proteus ammoniae* | Cystitis, enteritis, and omphalitis |
| 15. *Hemophilus influenzae* | Meningitis and influenza |
| 16. *Moraxella bovis* | Infectious ketatitis |
| 17. *Leptospira spp* (various strains) | Abortion, strangles, and numerous others |
| 18. *Spherophorus necrophorus* | Calf diphtheria |
| 19. *Shigella dysenteriae* | Dysentery |
| 20. *Actinomyces bovis* | Lumpy jaw |
| 21. *Bacillus anthracis* | Anthrax |
| 22. *Streptococcus spp* (various strains) | Abortion, strangles, and numerous others |
| 23. *Corynebacterium spp* | Caseous lymphadenitis, bronchopneumonia, and numerous others |
| 24. *Erysipelothrix insidiosa* | Swine erysipelas |

Of the bacteria set forth in Table I above, most pertain to disorders encountered in veterinary medicine. However, *Neisseria gonorrhoeae* and *Neisseria menignitidis* in Table I are human pathogens only, and are given in Table I as examples of bacteria which may be used to produce human vaccines in accordance with the present invention. This is done as a further example that, if desired, the present invention may be used to provide human vaccines as well as animal vaccines.

While not exhaustive, the list of pathogenic bacteria given in Table I above (with the exceptions of *Neisseria gonorrhoeae* and *Neisseria menignitidis*) and the corresponding associated disorders, is believed to be a fair representation of some of the more common diseases in veterinary medicine. It should be understood that, while specific species of bacteria has been given for each genus in Table I above, there are many examples given in Table I wherein two or more species are important pathogens, and these are well known to those of ordinary skill in the art.

In this regard, it is noted that the term "spp," as used as a suffix in Table I above and as used in the art, refers to the fact that many bacteria have more than one speies present, but that the precise identification of those particular species and their proportionsare unknown. Further, the term "sp" is also used in the art as a suffix to connote that one particular species of that bacteria is involved in the bacterial culture, but that the precise identification of that particular species is also unknown. Thus, where the term "sp" or "spp" is used herein to describe a particular bacterium, it will be appreciated that any and all species of the genus of that bacterial family are meant to be included within the scope of that term, and it should not be considered as limited to one or more particular species.

It has been found that the most successful application of the present invention to date has been achieved using gram negative bacteria. Examples of such gram negative bacteria are set forth as Bacteria Nos. 1–19 in Table I. However, the present invention can also be used to prepare vaccines from gram positive bacteria, and Bacteria Nos. 20–24 in Table I include examples of such gram positive bacteria. Further, it is anticipated that the present invention may have application with respect to antigens or pathogens other than those found in bacteria. For example, it is anticipated that pathogens such as rickettsiae and fungi may also be extracted in accordance with the procedures of the present invention for usage in vaccines.

Once one or more particular types of bacteria have been selected for the preparation of a vaccine in accordance with the present invention, the bacterial cells are contacted with a detergent so as to extract from the bacterial cells antigens responsible for inducing protective immunity against the corresponding bacterially induced disease. It has been found that, by exposing the bacteria to a detergent, antigens responsible for inducing protective immunity against the bacterially induced disease are removed from the bacteria, while leaving the remaining major cellular components of the bacteria with the bacterial cells. Thus, the resultant antigen extract contains the antigens responsible for the protective immune response, but does not contain a significant excess of other cellular material from the bacterial cells which could otherwise prove toxic or induce harmful side effects.

Importantly, the detergent employed in the present invention is carefully chosen so as to have the following characteristics: (1) the detergent must be capable of removing the antigens responsible for the protective immune response from the bacterial cells without substantial denaturation of those antigens, and (2) the detergent must have a critical micelle concentration which is high enough to allow the detergent to be removed by dialysis to the degree necessary to avoid toxicity.

In this regard it should be noted that significant denaturation of the extracted antigens could greatly affect or even destroy the efficacy of the resultant animal vaccine. Thus, it is important that the antigens which are removed maintain their native form (antigenic structure) so as to induce an immune response in a vaccinated animal which will allow the animal to later recognize the same antigen on the surface of an intact bacterial pathogen. Further, if significant traces of the detergent used in the extraction step are present in the resultant vaccine after the dialysis step, such detergents may prove toxic to the animal vaccinated and/or may decrease the effectiveness of the vaccine. Hence, for purposes of the present invention, it is important that a detergent be employed having the abovementioned criteria.

Any detergents having the criteria mentioned above may be used to prepare vaccines in accordance with the present invention. Some examples of detergents which have been found to meet these criteria, and which are thus useful for purposes of the present invention, are set forth in Table II below. It will be understood that the detergents set forth in Table II are given by way of example only, and are not considered to be comprehensive or exhaustive of the possible detergents which may be used in the present invention. Thus, it will be realized that other detergents having the criteria set forth herein are also possible, and are within the scope of the present invention.

TABLE II

| Detergent | Critical Micelle Concentration (CMC) |
|---|---|
| 1. n-octyl-B-D-glucopyranoside | 25 mM |
| 2. n-octyl-B-D-thioglucopyranoside | 9 mM |
| 3. nonyl-B-D-glucopyranoside | 6.5 mM |
| 4. octanoyl-N-methylglucamide | Not yet determined but believed to be comparable to 1. above (about 25 mM) |
| 5. nonanoyl-N-methylglucamide | Not yet determined but believed to be comparable to 1. above (about 25 mM) |
| 6. decanoyl-N-methylglucamide | Not yet determined but believed to be comparable to 1. above (about 25 mM) |

As seen in Table II above, various n-alkyl-B-D-glucopyranosides such as n-octyl-B-D-glucopyranoside, n-octyl-B-D-thioglucopyranoside, and nonyl-B-D-glucopyranoside may be used as detergents in the present invention. (It will be understood that the capital letter "B" used in these detergent names is an abbreviation for the term "beta".) Further, various N-D-gluco-N-methylalkylamides such as octanoyl-N-methylglucamide, nonanoyl-N-methylglucamide, and decanoyl-N-methylglucamide may be used as detergents in accordance with the present invention.

As noted herein, it is important that the particular detergent employed in the present invention have a critical micelle concentration (CMC) which is sufficiently high to allow most, and preferably substantially all, of the detergent to be removed by dialysis. In general, it has been found that CMC values within the range of from about 5 millimoles per liter to about 35 millimoles per liter are sufficiently high to permit rapid removal of the detergent by dialysis in accordance with the present invention. As seen from Table II, the CMC values for each of the exemplary detergents set forth in Table II are well within this range. In the most presently preferred embodiment of the present invention, CMC values within the range of from about 9 millimoles per liter to about 25 millimoles per liter are used.

Anything that will help to increase the removability of the detergent from the antigen extract is desirable for purposes of the present invention. For example, in addition to the high CMC values set forth herein, it is also believed that relatively small micelle sizes are desirable and further facilitate removal of the detergent by dialysis.

Detergent 1 set forth in Table II is available from Sigma Chemical Company, St. Louis, Mo., under stock number 0-8001. Further, detergents 1, 2, and 3 in Table II may be purchased from Calbiochem-Behring, a division of American Hoechst Corporation, San Diego, Calif., under stock numbers 494459, 494461, and 488285, respectively. Detergents 4, 5, and 6 in Table II may also be purchased from Calbiochem-Behring under stock numbers 444926, 444930, and 444934, respectively, and are sold under the names Mega 8, Mega 9, and Mega 10, respectively. Thus, detergents which may be employed in the present invention are commercially available. At the present time, the N-D-gluco-N-methylalkylamide detergents are often preferred because of their relatively inexpensive cost.

Another criteria for consideration in choosing an appropriate detergent is its solubility in ionic or nonionic media. For example, detergents 1, 2, and 3 in Table II are soluble in nonionic media, whereas detergents 4, 5, and 6 in Table II are soluble in water and other ionic media. Hence, the particular selection of a detergent may also depend upon the nature of the media employed so that the detergent will be soluble therein.

Upon analysis, the bacterial extracts obtained using detergents in accordance with the present invention, appear to comprise outer membrane protein as the major component. This suggests that the bacterial extracts of the present invention contain primarily chemical substances which will be recognized as antigenic by an animal's immune system. Thus, although not entirely free from doubt, it is believed that the antigens responsible for eliciting a protective immune response against most bacteria are located on the surface or outer membrane of the bacterial cells.

The bacterial cell envelope of a typical gram negative bacterium is an immunochemically complex structure consisting of an inner cytoplasmic membrane, a rigid peptidoglycan layer, and an outer membrane. The outer membrane contains significant amounts of protein, phospholipid and lipopolysaccharide. It is possible that some of the protein present in the extracts of the present invention may be chemically bound to the lipids as well as the polysaccharides.

Although it is not precisely known which particular proteins are extracted and their exact location on the bacterial cells, it has been found that those proteins or antigens which are responsible for the protective immune response can be extracted in accordance with the present invention by a detergent as set forth herein, while minimizing the amount of immunologically useless cellular components in the resultant extract. Such extracts are relatively nontoxic compared to their prior art whole bacterial cell vaccine counterparts and elicit a much stronger immune response when injected into animals in the form of a vaccine.

Once the antigens responsible for the immune response have been extracted from the bacterial cells, the detergent is removed from the antigen extract by dialysis. The dialysis procedure used in the present invention is conventional and well within the skill of the art. However, the details of one presently preferred dialysis procedure which may be used in practicing the present invention is set forth hereinafter as part of Procedure I.

In the dialysis step, it is preferable to remove as much of the detergent as possible so as to avoid toxicity. By using detergents having relatively high CMC's as set forth herein, rapid and extensive, if not complete, removal of the detergent can be accomplished. Thus, as set forth hereinabove, it is important that the characteristics of the detergent used are such that the detergent can be removed as completely as possible by the dialysis procedure.

Once the detergent has been removed from the antigen extract by dialysis, the antigen extract is suitable for use in a vaccine. Preferably, however, before the antigen extract is administered to the animal to be immunized, a vaccine enhancing adjuvant is combined with the antigen extract so as to enhance the efficacy of the vaccine and the immune response elicited. Such adjuvants are well known in the art of vaccination.

Thus, the vaccine enhancing adjuvants which are employed in the present invention are substantially the same as those well-known and conventional adjuvants which are currently used in the preparation of known animal vaccines. For example, one well-known adjuvant, Freund's incomplete adjuvant, has been found satisfactory for purposes of the present invention and may be purchased from Difco Laboratories, Detroit, Mich. Also, the Ribi Adjuvant System (RAS) sold by Ribi ImmunoChem Research, Inc., Hamilton, Mont., is also suitable for usage as a vaccine enhancing adjuvant in the present invention. Again, it will be understood that the specific adjuvants mentioned herein are given by way of example only, and represent but a few examples of the many well-known adjuvants which may be employed in the present invention.

As noted, it is presently preferable to use an adjuvant with the vaccines prepared in accordance with the present invention, in order to enhance the immune response induced in the animals vaccinated. Adjuvants may act to do this in several different ways, one of which is to influence the processing of the antigens by the animal host so that they are more efficiently presented to the antigen-sensitive cells of the animal host. One way of doing this is to slow down the rate of antigen degradation by the animal host by mixing the antigen extract with an insoluble agent to form a depot from which the antigens are slowly released. Such depot forming substances may include either solid materials or water-in-oil emulsions. Both the exemplary adjuvants set forth herein, Freund's incomplete adjuvant and the RAS adjuvant, are water-in-oil emulsions.

The presence of the oil in such a water-in-oil adjuvant stimulates local chronic inflammation, and macrophages (the animal's host cells) are attracted to the site of injection. This is desirable since such macrophages are responsible for presenting the antigens to the animal's immune system in the manner necessary to stimulate the development of protective immunity.

The antigens are typically present in the aqueous phase of the water-in-oil emulsion, and are slowly released therefrom. As a result, the effective lifetime of the antigens within the adjuvant is considerably prolonged. For example, an antigen which may have a half life in an animal host of less than one day when administered without an adjuvant may have a half life of several weeks when suspended in a water-in-oil adjuvant Since the immune response is an antigen-driven process, the prolonged presence and activity of the antigens in the animal host results in a similar prolongation of the immune response exhibited by the animal.

One presently preferred procedure for preparing bacterial extract vaccines in accordance with the present invention is set forth in Procedure I below. It will be understood that the exemplary procedure set forth in Procedure I below is merely illustrative, and is merely provided as one example of a procedure which may be followed in order to prepare vaccines in accordance with the present invention.

Procedure I

First, the strain or strains of bacteria responsible for the disease to be immunized against are grown in broth comprising such nutrients as brain heart infusion plus 5% fetal bovine serum, or on solid media containing such nutrients as Columbia agar base plus 5% fetal bovine serum which is free of animal red blood cells. The bacterial growth is harvested by any suitable method such as centrifugation in the case of a broth media or by scraping with a sterile glass rod in the case of a solid media. The harvested bacterial cells are then preferably washed at least twice using, for example, about 30 milliliter (ml) aliquots of a sterile phosphate buffered saline solution having a pH of about 7.2, and then centrifuging at about 4° C. and at an acceleration of about $18,000 \times g$ (18,000 times gravity) after each wash for about 20 minutes. A 0.1M phosphate buffered saline solution which may be used in this regard is prepared by mixing about 2.484 grams of $NaH_2PO_4$, about 11.644 grams of $Na_2HPO_4$, and about 9 grams of NaCl in 1 liter of deionized distilled water ($DDH_2O$) until dissolved, and the pH of the resultant solution is adjusted to 7.2 by the dropwise addition of concentrated hydrochloric acid (HCl).

After centrifuging, the packed bacterial cells in the phosphate buffered saline solution are transferred to a 15 ml conical centrifuge tube where they are again centrifuged at about 4° C. and at about 2,000 x g for about 25 minutes. The resultant supernatant is carefully removed and the packed bacterial cell volume is formed into a pellet. If desired, the bacterial cell pellet may be frozen, for example at a temperature of about −80° C., and then stored until needed for the preparation of a vaccine.

When it is desired to prepare the vaccine, the bacterial cell pellet (which, if frozen, is preferably first warmed to room temperature) is extracted using a 2% (by weight) solution of an appropriate detergent (such as any detergent found in Table II) in a 10 millimolar (10 mM) solution of Tris buffer in deionized distilled water ($DDH_2O$) having a pH of about 7.4. The 10 mM Tris buffer solution may be prepared by dissolving about 1.21 grams of $C_4H_{11}NO_3$ in one liter of $DDH_2O$, and adjusting the pH of the resultant solution to 7.4 by the dropwise addition of concentrated HCl. Enough detergent is then dissolved in the Tris buffer solution to yield a 2% by weight solution of the detergent. For each volume of packed bacterial cells to be extracted, 19 volumes of the detergent solution should be prepared. (For example 0.5 ml of packed bacterial cells should be extracted using 9.5 ml of detergent solution.)

To perform the extraction, the bacterial cells are completely suspended in the detergent solution by gently mixing with a Pasteur pipet or a 3 ml syringe equipped with a 16 gauge needle. The bacterial cell suspension thus mixed is then incubated for about two hours at room temperature in a small beaker, with slow continuous stirring, provided for example, by a Teflon coated stir bar and a magnetic stirrer. The resultant incubated suspension is then centrifuged at about 4° C. and at about $5,000-10,000 \times g$ for about 30 minutes.

The supernatant from the centrifuged bacterial cell suspension contains the antigens to be used in the vaccine. Hence, the supernatant is carefully placed in a presoaked dialysis tubing (for example, presoaked in $DDH_2O$) having a molecular weight cutoff of approximately 6-12 K (6,000 to 12,000 daltons). Subsequently, the supernatant is dialyzed against a 10 mM Tris buffer at about 4° C. with slow stirring for about 48 hours.

In the above dialysis step, approximately 300 ml of cold (about 4° C.) Tris buffer dialysate is used for each 10 ml of bacterial extract. The dialysate is preferably changed after about 18 hours, and again at 24 hours, using 300 ml aliquots of the cold Tris buffer dialysate each time. After the 48 hour period has expired, the dialyzed extract is transferred to preparative centrifuge tubes and is centrifuged at about 4° C. and at about $100,000 \times g$ for about one hour. The resultant supernatant is then collected and measured into sterile serum bottles and then shell frozen within a temperature range of about −15° C. to about −80° C. for lyophilization.

If desired a small aliquot of the resultant supernatant may be reserved for protein analysis by Lowry's protein determination. After the extracts are lyophilized, they are stored at about −20° C. until needed. When it is desired to use the extract in a vaccine, the extract is preferably warmed to room temperature and mixed with about 1 ml of an appropriate adjuvant per ml of extract, such as Freund's incomplete adjuvant or RAS adjuvant. The resultant vaccine is then ready for administration.

Once a vaccine has been prepared in accordance with Procedure I above or in accordance with any other procedure within the scope of the present invention, the vaccine is then administered to the animal or animals to be immunized. Such administration is preferably carried out by either intramuscular injection or subcutaneous injection. The precise dosages used, however, like with any other vaccines, must be determined on a case by case basis.

The immune response, like other biological phenomena, is seldom equal among different members of a vaccinated population. It is difficult, therefore, to provide precise dosages and immunization schedules which will apply to all populations across the board and which will be suitable for all antigens. Thus, some field trials are typically necessary in order to define a precise acceptable dosage range for a particular vaccine in a particular population. However, for purposes of the present invention, dosages of from about 1 mg of protein antigen to about 2 mg of protein antigen per animal per vaccination are generally suitable, although, of course, some situations may require somewhat higher or lower dosages.

For vaccines which were prepared from Actinobacillus sp (believed to be *Actinobacillus seminis*) for the purpose of treating ram epididymitis, a dosage range of about 0.5 milligrams (mg) to about 5 mg of protein antigen per animal per injection has been found suitable for certain populations of rams, with the most presently preferred dosage range being from about 1 mg to about 2.5 mg of protein antigen per animal per injection. Further, with respect to such vaccines for treating ram epididymitis, it has been found that an initial vaccination and a booster vaccination separated by about a 30 day period is often desirable. Further vaccinations will, of course, depend upon the population vaccinated.

In determining the amount of antigen which should be included within the vaccine so as to provide an immunologically effective vaccine in accordance with the present invention, several factors should be considered. Some of the more important factors include: (1) the particular species, phylogenetic relationship, and individual variation of the animals to be immunized; (2) the physical type, biochemical type, and stability of the antigens in the vaccine; (3) the particular adjuvant employed; (4) the type of immune response desired; and (5) the method of inoculation (e.g., intramuscular, subcutaneous, etc.).

With respect to the first consideration, including the particular species of animal to be immunized, some animals produce antibodies more easily than others. For example, rabbits, goats, and horses are believed to be among the best species for producing antibodies. Further, with respect to the phylogenetic relationship, the further the animal species is removed in evolutionary terms, the broader the immune response is likely to be in the animal, and only major differences between antigens may be recognized. Moreover, in random-bred stock, the peak antibody productions measured following a simple immunization procedure may vary as much as 500 times amongst individuals in the population.

With respect to the particular type of antigens the vaccine, some antigens are more soluble than others and are thus readily diluted out and catabolized, thereby tending to stimulate poor immune responses. Relatively high priming doses, may, in such instances, be needed. Most antigens can usually be given in a wide dosage range without inducing high or low dose tolerance. However, the dosage of polysaccharides may be more critical in this respect. Further, if the particular antigens are somewhat unstable, more complicated immunization schedules may become necessary.

With respect to the particular adjuvant used, water-in-oil emulsions given intramuscularly or subcutaneously typically stimulate an antibody response that rises slowly to a peak over two to three months and then tends to persist as a plateau. If different responses are desired, the dosages and adjuvants may require appropriate modification.

With respect to the type of immune response desired, highly specific antibodies are typically produced by relatively short immunization programs, and the production of antibodies against traces of any unwanted antigens in the vaccine may be minimized. Conversely, long immunization programs, such as those involving repeated application of the vaccine, produce less specific or more potently crossreacting antibodies. Thus, the length of the immunization program will necessarily depend upon the type of immune response desired.

Moreover, the desirability of repeating vaccinations may well depend upon the method of inoculation. When the vaccines are administered by intramuscular or subcutaneous injection, rapid access to the lymphatics is achieved with smaller amounts of vaccine, and frequent repetition of administration is often not necessary.

The following examples are given to illustrate various vaccines which have been made or may be made in accordance with the present invention. These examples are given by way of example only, and it is to be understood that the following examples are not comprehensive or exhaustive of the many different vaccines which can be prepared in accordance with the present invention.

EXAMPLE 1

In this example, a vaccine within the scope of the present invention was prepared using various Actinobacillus spp bacteria. The vaccine prepared in this example is suitable for vaccinating purebred ram lambs to protect against ram epididymitis.

In this example, 2 American Tissue Culture Collection (ATCC) cultures, namely *Actinobacillus seminis* and *Actinobacillus actinomycetemcomitans*, and 10 field isolates of Actinobacillus spp, believed to be primarily *Actinobacillus seminis*, were used. However, virtually any Actinobacillus sp or Actinobacillus spp bacteria could be used to prepare an Actinobacillus vaccine in accordance with this example. The various Actinobacillus spp bacterial cultures were grown on a Columbia blood agar base purchased from BBL Microbiology Systems, Becton Dickinson Company, Cockeysville, Md., to which was added about 5% by volume of a fetal bovine serum purchased from HyClone Sterile Systems, Logan, Utah. The bacterial cultures were grown for 72 hours at about 37° C. in an atmosphere of about 15% carbon dioxide ($CO_2$) and about 85% nitrogen ($N_2$) Subsequently, the bacterial growth from each culture was harvested by scraping with a sterile glass rod, and the harvested bacterial cells were combined and washed twice using successive 30 ml aliquots of a sterile phosphate buffered saline solution having a pH of about 7.2, and then centrifuged at about 4° C. and at about 18,000×g after each wash for about 20 minutes. A 0.1M phosphate buffered saline solution was used in this regard and was prepared by mixing about 2.484 grams of $NaH_2PO_4$, about 11.644 grams of $Na_2HPO_4$, and about 9 grams of NaCl in 1 liter of deionized distilled water ($DDH_2O$) until dissolved, and the pH of the resultant solution was adjusted to 7.2 by the dropwise addition of concentrated hydrochloric acid (HCl).

After centrifugation, the packed bacterial cells in the sterile phosphate buffered saline solution were transferred to a 15 ml conical centrifuge tube where they were again centrifuged at about 4° C. and at about 2,000 x g for about 25 minutes The resultant supernatant was carefully removed and the packed bacterial cell volume was formed into a pellet. The bacterial cell pellet was then extracted using a 2% (by weight) solution of n-octyl-B-D-glucopyranoside detergent, purchased from Sigma Chemical Co., St. Louis, Mo., under Stock No. 0-8001. This detergent solution was prepared as follows. First, a 10 millimolar (10 mM) solution of Tris buffer was prepared by dissolving about 1.21 grams of Tris buffer purchased from Sigma Chemical Co., St. Louis, Mo., under the tradename Trizma Base (Stock number T-1503), in about 1 liter of $DDH_2O$. The pH of the resultant solution was then adjusted to about 7.4 by the dropwise addition of concentrated HCl. Subsequently, about 2 grams of the n-octyl-B-D-glucopyranoside detergent were dissolved in about 100 ml of the Tris buffer solution.

The packed bacterial cells were divided into 0.5 ml aliquots, and were extracted using 9.5 ml aliquots of the detergent solution prepared. In this extraction step, the bacterial cells of each aliquot were completely suspended in the detergent solution by mixing with a Pasteur pipet. The bacterial cell suspension thus mixed was then incubated for about 2 hours at room temperature in a small beaker, with slow continuous stirring which was provided by a Teflon coated stir bar and a magnetic stirrer. The resultant incubated suspension was then centrifuged at about 4° C. and at about 5,000×g for about 30 minutes.

The supernatant from the centrifuged bacterial cell suspension contained the antigens to be used in the vaccine. Hence, the supernatant was carefully placed in a presoaked dialysis tubing (presoaked in $DDH_2O$) having a molecular weight cutoff of approximately 12 K. Subsequently, the supernatant was dialyzed against a 10 mM Tris buffer at about 4° C. with slow stirring for about 48 hours In the above dialysis step, approximately 300 ml of cold (4° C.) Tris buffer dialysate was used for each 10 ml of bacterial extract. The dialysate was changed after about 18 hours, and again at 24 hours, using 300 ml aliquots of the cold Tris buffer dialysate each time. After the 48 hour period had expired, the dialyzed extract was transferred to preparative centrifuge tubes and was centrifuged at about 4° C. and at about 100,000 x g for about one hour. The resultant supernatant was then collected and measured into sterile serum bottles purchased from Wheaton Scientific, Millville, N.J.

The supernatant in the sterile serum bottles was then shell frozen at about −20° C. for lyophilization using an FTS flexi-dry lyophilizor purchased from FTS Systems, Inc., Stoneridge, N.Y. for a period of about 8 to 16 hours, depending upon the volume of supernatant in each bottle. After the extracts were lyophilized, they were stored at about −20° C. until needed.

The extract of Example 1 above has been used in a vaccine for immunizing rams against ram epididymitis. In order to prepare the vaccine for administration, about 10 ml of Freund's incomplete adjuvant, purchased from Difco Laboratories, Detroit, Mich., was mixed with about 10 ml of the extract which had been warmed to room temperature. It was found that relatively large volumes of the bacterial extract could be mixed with relatively large volumes of the oil-based adjuvant using a Mickle high speed vibratory tissue disintegrator purchased from Brinkmann, a subsidiary of Sybron Corp., Cantiague Road, Westbury, N.Y. It was found that this apparatus successively mixed the aqueous-based vaccine with the oil-based adjuvant so as to provide a suitable vaccine for administration to the rams.

EXAMPLE 2

In this example, an antigen extract within the scope of the present invention was prepared from one strain of Actinobacillus sp bacteria in accordance with the procedure of Example 1, except that a 2% solution of n-octyl-B-D thioglucopyranoside was used in Example 2 instead of the 2% solution of n-octyl-B-D-glucopyranoside used in Example 1. Although, in Example 2, the antigen extract was not mixed with an adjuvant or administered as a vaccine, such may be done in accordance with the procedure of Example 1.

EXAMPLE 3

In this example, an antigen extract within the scope of the present invention was prepared from one strain of Actinobacillus sp bacteria in accordance with the procedure of Example 1, except that a 2% solution of nonyl-B-D-glucopyranoside was used in Example 3 instead of the 2% solution of n-octyl-B-D-glucopyranoside used in Example 1. Although, in Example 3, the antigen extract was not mixed with an adjuvant or administered as a vaccine, such may be done in accordance with the procedure of Example 1.

EXAMPLE 4

In this example, an antigen extract within the scope of the present invention was prepared from one strain of Actinobacillus sp bacteria in accordance with the procedure of Example 1, except that a 2% solution of octanoyl-N-methylglucamide was used in Example 4 instead of the 2% solution of n-octyl-B-D-glucopyranoside used in Example 1. Although, in Example 4, the antigen extract was not mixed with an adjuvant or administered as a vaccine, such may be done in accordance with the procedure of Example 1.

EXAMPLE 5

In this example, an antigen extract within the scope of the present invention was prepared from one strain of Actinobacillus sp bacteria in accordance with the procedure of Example 1, except that a 2% solution of nonanoyl-N-methylglucamide was used in Example 5 instead of the 2% solution of n-octyl-B-D-glucopyranoside used in Example 1. Although, in Example 5, the antigen extract was not mixed with an adjuvant or administered as a vaccine, such may be done in accordance with the procedure of Example 1.

EXAMPLE 6

In this example, an antigen extract within the scope of the present invention was prepared from one strain of Actinobacillus sp bacteria in accordance with the procedure of Example 1, except that a 2% solution of decanoyl-N-methylglucamide was used in Example 6 instead of the 2% solution of n-octyl-B-D-glucopyranoside used in Example 1. Although, in Example 6, the antigen extract was not mixed with an adjuvant or administered as a vaccine, such may be done in accordance with the procedure of Example 1.

EXAMPLE 7

In this example, an antigen extract within the scope of the present invention was prepared from *Brucella ovis* in accordance with the procedure of Example 1, substituting *Brucella ovis* bacteria for the Actinobacillus spp bacteria used in Example 1. Although, in Example 7, the antigen extract was not mixed with an adjuvant or administered as a vaccine, such may be done in accordance with the procedure of Example 1.

EXAMPLE 8

In this example, an antigen extract within the scope of the present invention was prepared from a Pasteurella bacterial strain, namely, *Pasteurella multocida,* in accordance with the procedure of Example 1, substituting *Pasteurella multocida* bacteria for the Actinobacillus spp bacteria used in Example 1. Although, in Example 8, the antigen extract was not mixed with an adjuvant or administered as a vaccine, such may be done in accordance with the procedure of Example 1.

EXAMPLE 9

In this example, an antigen extract within the scope of the present invention (suitable for human use) was prepared from two strains of *Neisseria gonorrhoeae* bacteria. This antigen extract was prepared in accordance with the procedure of Example 1, except that two strains of *Neisseria gonorrhoeae* bacteria were substituted for the Actinobacillus Spp bacteria used in Example 1.

EXAMPLE 10

In this example, a vaccine within the scope of the present invention (suitable for human use) may be prepared from *Neisseria menignitidis* bacteria. This vaccine is prepared in accordance with the procedure of Example 1, except that *Neisseria menignitidis* bacteria are substituted for the Actinobacillus spp bacteria used in Example 1.

EXAMPLE 11

In this example, a vaccine within the scope of the present invention may be prepared from *Campylobacter fetus* bacteria. This vaccine is prepared in accordance with the procedure of Example 1, except that *Campylobacter fetus* bacteria are substituted for the Actinobacillus spp bacteria used in Example 1.

EXAMPLE 12

In this example, a vaccine within the scope of the present invention may be prepared from *Klebsiella pneumoniae* bacteria This vaccine is prepared in accordance with the procedure of Example 1, except that *Klebsiella pneumoniae* bacteria are substituted for the Actinobacillus spp bacteria used in Example 1.

EXAMPLE 13

In this example, a vaccine within the scope of the present invention may be prepared from *Escherichia coli* bacteria. This vaccine is prepared in accordance with the procedure of Example 1, except that *Escherichia coli* bacteria are substituted for the Actinobacillus spp bacteria used in Example 1.

EXAMPLE 14

In this example, a vaccine within the scope of the present invention may be prepared from *Pseudomonas aeruginosa* bacteria. This vaccine is prepared in accordance with the procedure of Example 1, except that *Pseudomonas aeruginosa* bacteria are substituted for the Actinobacillus spp bacteria used in Example 1.

EXAMPLE 15

In this example, a vaccine within the scope of the present invention may be prepared from *Hemophilus somnus* bacteria. This vaccine is prepared in accordance with the procedure of Example 1, except that *Hemophilus somnus* bacteria are substituted for the Actinobacillus spp bacteria used in Example 1.

EXAMPLE 16

In this example, a vaccine within the scope of the present invention may be prepared from Salmonella spp bacteria. This vaccine is prepared in accordance with the procedure of Example 1, except that Salmonella spp bacteria are substituted for the Actinobacillus spp bacteria used in Example 1.

EXAMPLE 17

In this example, a vaccine within the scope of the present invention may be prepared from *Bacteroides nodosus* bacteria. This vaccine is prepared in accordance with the procedure of Example 1, except that *Bacteroides nodosus* bacteria are substituted for the Actinobacillus spp bacteria used in Example 1.

EXAMPLE 18

In this example, a vaccine within the scope of the s z present invention may be prepared from *Bordetella bronchiseptica* bacteria. This vaccine is prepared in accordance with the procedure of Example 1, except that *Bordetella bronchiseptica* bacteria are substituted for the Actinobacillus spp bacteria used in Example 1.

EXAMPLE 19

In this example, a vaccine within the scope of the present invention may be prepared from *Proteus ammoniae* bacteria. This vaccine is prepared in accordance with the procedure of Example 1, except that *Proteus ammoniae* bacteria are substituted for the Actinobacillus spp bacteria used in Example 1.

EXAMPLE 20

In this example, a vaccine within the scope of the present invention may be prepared from *Hemophilus influenzae* bacteria. This vaccine is prepared in accordance with the procedure of Example 1, except that *Hemophilus influenzae* bacteria are substituted for the Actinobacillus spp bacteria used in Example 1.

EXAMPLE 21

In this example, an antigen extract within the scope of the present invention was prepared from two strains of *Moraxella bovis* bacteria. This antigen extract was prepared in accordance with the procedure of Example 1, except that two strains of *Moraxella bovis* bacteria were substituted for the Actinobacillus spp bacteria used in Example 1.

EXAMPLE 22

In this example, a vaccine within the scope of the present invention may be prepared from Leptospira spp bacteria. This vaccine is prepared in accordance with the procedure of Example 1, except that Leptospira spp bacteria are substituted for the Actinobacillus spp bacteria used in Example 1.

EXAMPLE 23

In this example, a vaccine within the scope of the present invention may be prepared from *Spherophorus necrophorus* bacteria. This vaccine is prepared in accordance with the procedure of Example 1, except that *Spherophorus necrophorus* bacteria are substituted for the Actinobacillus spp bacteria used in Example 1.

EXAMPLE 24

In this example, a vaccine within the scope of the present invention may be prepared from *Shigella dysenteriae* bacteria. This vaccine is prepared in accordance with the procedure of Example 1, except that *Shigella dysenteriae* bacteria are substituted for the Actinobacillus spp bacteria used in Example 1.

EXAMPLE 25

In this example, a vaccine within the scope of the present invention may be prepared from *Actinomyces bovis* bacteria. This vaccine is prepared in accordance with the procedure of Example 1, except that *Actinomyces bovis* bacteria are substituted for the Actinobacillus spp bacteria used in Example 1.

EXAMPLE 26

In this example, a vaccine within the scope of the present invention may be prepared from *Bacillus anthracis* bacteria. This vaccine is prepared in accordance with the procedure of Example 1, except that *Bacillus anthracis* bacteria are substituted for the Actinobacillus spp bacteria used in Example 1.

EXAMPLE 27

In this example, a vaccine within the scope of the present invention may be prepared from Streptococcus spp bacteria. This vaccine is prepared in accordance with the procedure of Example 1, except that Streptococcus spp bacteria are substituted for the Actinobacillus spp bacteria used in Example 1.

EXAMPLE 28

In this example, an antigen extract within the scope of the present invention was prepared from two species of Corynebacterium bacteria (*Corynebacterium parvum* and *Corynebacterium equi*). This antigen extract was prepared in accordance with the procedure of Example 1, except that two species of Corynebacterium bacteria were substituted for the Actinobacillus spp bacteria used in Example 1.

EXAMPLE 29

In this example, a vaccine within the scope of the present invention may be prepared from *Erysipelothrix insidiosa* bacteria. This vaccine is prepared in accordance with the procedure of Example 1, except that *Erysipelothrix insidiosa* bacteria are substituted for the Actinobacillus spp bacteria used in Example 1.

It will be recognized that vaccines comprising a combination of two or more different antigen extracts are also within the scope of the present invention, and are sometimes preferable. For example, some bacterially induced diseases are caused by more than one type of bacteria. Hence, in order to provide the most complete or ideal vaccine in such an instance, it is desirable to include in the vaccine administered to the animals antigen extracts from each of the responsible bacteria.

For example, in vaccinating against epididymitis in rams, such a combination vaccine may be desirable. In this regard, there are two main types of sheep producing operations in the United States, namely, range and purebred operations. The purebred operations concentrate on producing ram lambs that will be purchased by range producers to breed ewes on pasture. Although epididymitis occurs in rams raised in both range and purebred operations, ram epididymitis is caused almost exclusively by *Bruella ovis* in range flocks, while either Actinobacillus spp or *Hemophilus somnus* are the two primary bacteria which cause ram epididymitis in purebred production units. Since many purebred ram lambs will at some point become mature range rams, it would be most desirable to prepare a vaccine which will provide immune protection against all three of these bacteria. Thus, a more complete or ideal vaccine to protect rams against epididymitis during the course of their reproductive usefulness may often be a combination vaccine containing antigen extracts from all three of these bacteria.

Following is an example of one such combination vaccine which may be prepared in accordance with the present invention. Again, it will be appreciated that the following example is given by way of example only, and that many other combination vaccines may be prepared in accordance with the present invention for immunization against diseases caused by two or more different bacteria, including, for example, some of the diseases listed in Table I above.

EXAMPLE 30

In this example, a combination vaccine within the scope of the present invention may be prepared which contains antigen extracts from Actinobacillus spp, *Brucella ovis*, and *Hemophilus somnus* bacteria. To prepare this combination vaccine, approximately equal volumes of the antigen extracts from each of Examples 1, 7, and 15 are mixed together. The resultant combined antigen extract is then preferably combined with about an equal volume of an adjuvant in accordance with the procedure of Example 1, and may then be administered to the rams to be vaccinated.

The following Example 31 summarizes the results of a clinical evaluation which has been conducted wherein a certain vaccine prepared in accordance with the present invention was administered to certain animals, and the presence of antibodies produced and/or the incidence of bacterially induced disease was monitored. The following example clearly evidences the utility and effectiveness of the vaccine tested.

EXAMPLE 31

In this example, a vaccine was prepared from a single Actinobacillus sp isolate (believed to be *Actinobacillus seminis*) in accordance with the procedure of Example 1. Approximately equal volumes of the vaccine and Freund's incomplete adjuvant were then mixed and administered to 10 adult Navajo rams. In this regard, five of the rams received the vaccine by intramuscular injection, while the other five rams received the vaccine by subcutaneous injection.

Each ram received an initial 2 ml vaccination containing about 1 ml of antigen extract and about 1 ml of adjuvant, and a booster vaccination of like composition was administered to each of the rams 26 days later using the same method of administration used initially. The rams were monitored every other day for one week following the initial and booster vaccinations for development of adverse reactions to the test vaccine. Blood was collected from each ram just before the initial vaccination on Jan. 18, 1985, and subsequently on Feb. 13, 1985 just before the booster vaccination, as well as on Mar. 5, 1985 and June 13, 1985. Serum was obtained from each blood sample and stored frozen at −80° C. for future use and evaluation.

During the course of the experiment, no significant adverse reactions following administration of the vaccine were noted in any of the rams. Body temperature remained normal, and all rams continued to eat and drink. Three of the five rams receiving the vaccine by subcutaneous injection developed nodules at the injection site within a few days after receiving the vaccine. However, in no case did the nodules abscess or rupture to the surface, and all nodules disappeared after about four weeks. Nodules did not develop in any of the five rams which received the vaccine by intramuscular injection.

Antibody levels were monitored for each of the rams using the well-known enzyme-linked immunosorbent assay (ELISA) during the course of the experiment. The results of this experiment suggest that the vaccines were indeed effective in eliciting the production of antibodies against antigens on the outer membrane of Actinobacillus sp. The antibody levels as determined by ELISA values against Actinobacillus sp observed just before the initial and booster vaccinations of this experiment are set forth in Table III below.

TABLE III

ELISA values for paired sera samples from 10 adult Navajo rams.

| | ELISA VALUES | |
|---|---|---|
| Ram Number | Pre-initial vaccination sera (January 18, 1985) | Pre-booster vaccination sera (February 13, 1985) |
| Subcutaneous Vaccination | | |
| 410 | 59 | 220 |
| 422 | 201 | 431 |
| 431 | 57 | 327 |
| 434 | 35 | 265 |
| BF/WTK | 73 | 298 |
| Intramuscular Vaccination | | |
| 418 | 75 | 337 |
| 419 | 76 | 612 |
| 416 | 58 | 486 |
| 404 | 124 | 564 |
| 421 | 48 | 526 |

In Table III above, all sera samples were tested at a 1:400 dilution (diluted with sterile physiological buffered saline solution (pH 7.2)). Antibody activity is considered positive for ELISA values greater than 80. As shown from Table III, most sera samples show at least a fourfold increase in antibody titer against the ram epididymitis pathogen, Actinobacillus sp, 26 days following the initial vaccination using the bacterial extract preparation of this example.

In Table III above and in all other tables involving ELISA values, the ELISA values represent spectrometric readings made at 490 nanometers. In this regard, the absorbance of the sterile physiological buffered saline solution was blanked to zero by calibrating the spectrophotometer used to make the readings, and the absorbance at 490 nanometers was measured for each of the sera samples.

As reported in Table IV below, the antibody activity against Actinobacillus sp, in varying dilutions of the sheep sera was also determined by the ELISA test 20 days following the booster vaccination. At this point of the experiment, antibody activity is considered positive for ELISA values greater than 40. As seen in Table IV below, in 9 of 10 of the rams, antibody activity against the ram lamb epididymitis pathogen, Actinobacillus sp, was still positive after the sera were diluted 1:3200.

TABLE IV

| | ELISA VALUES (Sera Dilutions) | | | |
|---|---|---|---|---|
| Ram Number | 1:50 | 1:400 | 1:1600 | 1:3200 |
| Subcutaneous Vaccination | | | | |
| 410 | 631 | 313 | 108 | 40 |
| 422 | 708 | 404 | 177 | 151 |
| 431 | 731 | 633 | 340 | 171 |
| 434 | 688 | 392 | 187 | 102 |
| BF/WTK | 649 | 529 | 325 | 226 |
| Intramuscular Vaccination | | | | |
| 418 | 800 | 430 | 210 | 134 |
| 419 | 799 | 567 | 275 | 213 |
| 416 | 494 | 358 | 137 | 89 |
| 404 | 881 | 645 | 282 | 146 |
| 421 | 778 | 289 | 173 | 102 |

Antibody titers using the ELISA test were also calculated for sera samples taken on three different dates from one of the subcutaneously vaccinated rams, and the results are tabulated in Table V below.

TABLE V

| | ELISA Antibody Titer Sera Samples - 1985 | | |
|---|---|---|---|
| Ram Number | January 18 | February 13 | March 5 |
| 431 | <1:400 | 1:6,400 | 1:12,800 |

In Table V above, it will be understood that the term "antibody titer" is a measure of the positive antibody activity in the sera samples tested, and that the various sera samples were diluted several times in order to determine the highest dilution where positive antibody activity was still present. Thus, an antibody titer value of 1:400 in Table V above means that the serum sample was diluted 400 times and still had positive antibody activity As seen in Table V, there was a progressive increase in the antibody titer against the ram lamb epididymitis organism, Actinobacillus sp, following the initial and booster vaccination of ram number 431.

The persistence of antibody activity against Actinobacillus sp was monitored in two of the vaccinated rams from four of the different sera samples taken. The results of these tests are tabulated in Table VI below.

TABLE VI

| | ELISA VALUES Sera Sample dates - 1985 | | | |
|---|---|---|---|---|
| Ram Number | January 18 | February 13 | March 5 | June 6 |
| Subcutaneous Vaccination | | | | |
| 434 | 12 | 211 | 249 | 131 |
| Intramuscular Vaccination | | | | |
| 419 | 13 | 94 | 202 | 116 |

All sera samples shown in Table VI were diluted 1:400, and antibody activity is consider positive for ELISA values greater than 20. As seen in Table VI above, antibody activity against the ram lamb epididymitis pathogen, Actinobacillus sp, persisted strongly to at least June 6, 1985, following the initial vaccination on Jan. 18, 1985 and a booster vaccination on Feb. 13, 1985. Antibody activity was not monitored after June 6, 1985.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for preparing a veterinary vaccine which may be used in the immunization of sheep against bacterially induced lamb epididymitis, the method comprising the steps of:
   (a) obtaining Actinobacillus spp and *Hemophilus somnus* bacteria responsible for the lamb epididymitis against which immunity is sought;
   (b) contacting the Actinobacillus spp and *Hemophilus somnus* bacteria with n-octyl-β-D-glucopyranoside detergent which is capable of extracting antigens from the outer membrane of the bacteria without substantial denaturation of the antigen and while leaving the remaining major cellular components of the bacteria with the bacteria cells;
   (c) dialyzing the antigen-detergent mixture to substantially remove the n-octyl-β-D-glucopyranoside detergent from the antigen, leaving an antigen extract such that the antigen extract is not toxic to the sheep when used as a vaccine; and
   (d) forming a veterinary vaccine from the antigen extract without further antigen purification processing steps, said forming step including the step of combining the antigen extract with a vaccine enhancing adjuvant.

2. A method for immunizing sheep against bacterially induced lamb epididymitis, the method comprising the steps of:
   (a) obtaining Actinobacillus spp and *Hemophilus somnus* bacteria responsible for the lamb epididymitis against which immunity is sought;
   (b) contacting the Actinobacillus spp and *Hemophilus somnus* bacteria with n-octyl-β-D-glucopyranoside detergent which is capable of extracting antigens from the outer membrane of the bacteria without substantial denaturation of the antigen and while leaving the remaining major cellular components of the bacteria with the bacteria cells;
   (c) dialyzing the antigen-detergent mixture to substantially remove the n-octyl-β-D-glucopyranoside detergent from the antigen leaving an antigen extract;
   (d) forming a veterinary vaccine from the antigen extract without further antigen purification processing steps, said forming step including the step of combining the antigen extract with a vaccine enhancing adjuvant; and
   (e) administering to the sheep an immunologically effective amount of the veterinary vaccine.

3. A veterinary vaccine which may be used in the immunization of sheep against bacterially induced lamb epididymitis prepared by the method comprising the steps of:
   (a) obtaining Actinobacillus spp and *Hemophilus somnus* bacteria responsible for the lamb epididymitis against which immunity is sought;
   (b) contacting the Actinobacillus spp and *Hemophilus somnus* bacteria with n-octyl-β-D-glucopyranoside detergent which is capable of extracting antigens from the outer membrane of the bacteria without substantial denaturation of the antigen and while leaving the remaining major cellular components of the bacteria with the bacteria cells;
   (c) dialyzing the antigen-detergent mixture to substantially remove the n-octyl-β-D-glucopyranoside detergent from the antigen, leaving an antigen extract such that the antigen extract is not toxic to the sheep when used as a vaccine; and
   (d) forming a veterinary vaccine from the antigen extract without further antigen purification processing steps, said forming step including the step of combining the antigen extract with a vaccine enhancing adjuvant.

* * * * *

UNITED STATES PATENT AND TRADEMARK OFFICE
CERTIFICATE OF CORRECTION

PATENT NO. : 4,981,685

DATED : January 1, 1991

INVENTOR(S) : MARK C. HEALEY

It is certified that error appears in the above-identified patent and that said Letters Patent is hereby corrected as shown below:

```
Column 5, line 58, "proportionsare" should be --proportions are--
Column 9, line 44, after "adjuvant" insert --.--
Column 12, line 6, after "antigens" insert --used in--
Column 13, line 3, after "(N_2)" insert --.--
Column 13, line 22, after "minutes" insert --.--
Column 13, line 59, after "hours" insert --.--
Column 16, line 1, after "bacteria" insert --.--
Column 16, line 47, delete "s z"
```

Signed and Sealed this

Twenty-second Day of September, 1992

*Attest:*

DOUGLAS B. COMER

*Attesting Officer*     *Acting Commissioner of Patents and Trademarks*